US008773526B2

(12) United States Patent
Bryll

(10) Patent No.: US 8,773,526 B2
(45) Date of Patent: Jul. 8, 2014

(54) EDGE DETECTION USING STRUCTURED ILLUMINATION

(75) Inventor: Robert K. Bryll, Bothell, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 684 days.

(21) Appl. No.: 12/972,386

(22) Filed: Dec. 17, 2010

(65) Prior Publication Data

US 2012/0154571 A1 Jun. 21, 2012

(51) Int. Cl.
*H04N 5/253* (2006.01)

(52) U.S. Cl.
USPC .......................................................... 348/94

(58) Field of Classification Search
None
See application file for complete search history.

(56) References Cited

U.S. PATENT DOCUMENTS

| | | | |
|---|---|---|---|
| 5,101,295 A | 3/1992 | Lichtman | |
| 5,323,009 A | 6/1994 | Harris | |
| 5,452,090 A | 9/1995 | Progler | |
| 5,659,384 A | 8/1997 | Ina | |
| 6,288,382 B1 | 9/2001 | Ishihara | |
| 6,542,180 B1 | 4/2003 | Wasserman | |
| 6,665,066 B2 | 12/2003 | Nair | |
| 6,917,421 B1 | 7/2005 | Wihl | |
| 6,940,610 B2 | 9/2005 | Prinzhausen | |
| 7,016,525 B2 * | 3/2006 | Gladnick | 382/141 |
| 7,109,458 B2 | 9/2006 | Fairley | |
| 7,142,315 B1 | 11/2006 | Lange | |
| 7,199,882 B2 | 4/2007 | Svetkoff | |
| 7,324,682 B2 | 1/2008 | Wasserman | |
| 7,329,860 B2 | 2/2008 | Feng | |
| 7,330,305 B2 | 2/2008 | Harris | |
| 7,454,053 B2 | 11/2008 | Bryll | |
| 2003/0185430 A1 * | 10/2003 | Theobald et al. | 382/141 |
| 2006/0017720 A1 | 1/2006 | Li | |
| 2007/0183666 A1 * | 8/2007 | Ding | 382/199 |
| 2007/0258086 A1 * | 11/2007 | Bleeker et al. | 356/237.4 |
| 2008/0151194 A1 * | 6/2008 | Segev | 353/28 |
| 2010/0158343 A1 | 6/2010 | Bryll | |
| 2010/0245093 A1 | 9/2010 | Kobetski | |
| 2010/0302599 A1 * | 12/2010 | Goto et al. | 358/3.27 |

OTHER PUBLICATIONS

Campbell, S.R., "Autofocus Video Tool and Method for Precise Dimensional Inspection," U.S. Appl. No. 12/608,943, filed Oct. 29, 2009.

(Continued)

*Primary Examiner* — Sath V Perungavoor
*Assistant Examiner* — Kate Luo
(74) *Attorney, Agent, or Firm* — Christensen O'Connor Johnson Kindness PLLC

(57) ABSTRACT

A machine vision inspection system (MVIS) and a related light stripe edge feature location method are disclosed. The MVIS comprises a control system, a light stripe projection system, an imaging system, and a user interface. In a region of interest including the edge feature, the light stripe projection system focuses a light stripe transverse to the edge direction and across the edge feature, such that the light stripe has a changing stripe intensity profile along the light stripe. The imaging system acquires an image of the light stripe and the control system analyzes the image to determine the location of the edge feature based on a changing light intensity profile along the stripe. The method may be implemented in an edge detection video tool. The method may be advantageous for inspecting highly textured, beveled, chamfered, rounded or damaged edges, for example.

24 Claims, 6 Drawing Sheets

(56) References Cited

OTHER PUBLICATIONS

Larson, J.M., et al., "Resonant Scanning in Laser Confocal Microscopy," © 2000-2010, Nikon MicroscopyU.com, <www.microscopyu.com/articles/confocal/resonantscanning.html> [retrieved Jan. 4, 2011], 14 pages.

Poher, V., et al., "Optical Sectioning Microscopes With No Moving Parts Using a Micro-Stripe Array Light Emitting Diode," Optics Express 15(18):11196-11206, Sep. 2007.

"QVPAK 3D CNC Vision Measuring Machine: Operation Guide," Version 2.0, Manual No. 4911GB, Series No. 359, Mitutoyo Corporation & Micro Encoder Inc., Kanagawa, Japan, Sep. 1996, 86 pages.

"QVPAK 3D CNC Vision Measuring Machine: User's Guide," Version 7.1, 2d ed., Manual No. 99MCB225A, Series No. 359, Mitutoyo Corporation & Micro Encoder Inc., Kanagawa, Japan, Sep. 2003, 370 pages.

Sabharwal, Y.S., et al. "Slit-Scanning Confocal Microendoscope for High-Resolution In Vivo Imaging," Applied Optics 38(34):7133-7144, Dec. 1999.

* cited by examiner

EDGE DETECTION USING STRUCTURED ILLUMINATION

FIELD OF THE INVENTION

The invention relates generally to machine vision inspection systems, and more particularly to methods of edge detection on workpiece surfaces.

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro Model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 (the '180 patent) teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

The machine control instructions, including the specific inspection event sequence (i.e., how to acquire each image and how to analyze/inspect each acquired image), are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs". Video tools may include, for example, edge/boundary detection tools, autofocus tools, shape or pattern matching tools, dimension measuring tools, and the like.

Various methods are known for locating edge features in workpiece images. For example, various algorithms are known which apply brightness gradient operators to images which include an edge feature to determine its location, e.g., a Canny Edge detector or a differential edge detector. Such edge detection algorithms may be included in the machine vision inspection systems which also use carefully configured illumination and/or special image processing techniques to enhance brightness gradients or otherwise improve edge location accuracy and repeatability. Nevertheless, edge features located near a highly textured surface or located at one edge of a surface feature, such as a chamfer, have proven difficult for unskilled machine vision users to inspect reliably when using known techniques for edge detection. An improved edge detection system and/or method which may be used to reliably inspect such edges would be desirable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A system and method for determining a location of an edge feature of a workpiece using a machine vision inspection system is provided. Determining the location of an edge feature in an image may also be referred to herein as edge detection. Edge detection often refers to edge discovery or identification of edges in the field of image processing, and may or may not encompass determining their precise location. However, it should be appreciated that the systems and methods disclosed herein are particularly valuable for precisely determining the location of an edge in various embodiments (e.g., with sub-pixel accuracy, in some embodiments or applications), regardless of whether they are characterized as edge detection operations or edge location operations.

The machine vision inspection system comprises a control system, a light stripe projection system, an imaging system, and a user interface usable to define a sequence of operations usable to determine the location of the edge feature. The method, in various embodiments may generally comprise steps, including: (A) positioning the edge feature in a field of view of a machine vision inspection system; (B) focusing the imaging system at an imaging focus plane at a height corresponding to the edge feature; and (C) determining the edge feature location, wherein determining the edge feature location comprises: (C1) operating the light stripe projection system to project at least one light stripe oriented to extend across the edge feature and focused such that a height change across the edge feature causes at least one of a changing width and a changing intensity along the light stripe; (C2) operating the imaging system to acquire an image of the at least one light stripe at the imaging focus plane; and (C3) analyzing the acquired image of the at least one light stripe in the region of interest and determining the location of at least a portion of the edge feature based on a changing characteristic along the light stripe that corresponds to at least one of the changing width (e.g., a width characterizing a transverse light intensity profile), and the changing intensity (e.g., a peak intensity of a transverse light intensity profile, or other representative intensity) along the light stripe.

The method, in some particular embodiments, may comprise steps including: (a) positioning the edge feature in a field of view of a machine vision inspection system; (b) focusing the imaging system at an imaging focus plane at a height corresponding to the edge feature; (c) defining a region of interest including the edge feature using the user interface; (d) determining an edge direction corresponding to a direction along the edge feature in the region of interest; and (e) determining the edge feature location based on operations, comprising: (e1) operating the light stripe projection system to project at least one light stripe oriented transverse to the determined edge direction in the region of interest, and extending across the edge feature; (e2) operating the light stripe projection system to focus the at least one light stripe at a light stripe focus plane at a height corresponding to the edge feature, such that a height change across the edge feature causes a changing stripe intensity profile (e.g., a changing transverse intensity profile) along the light stripe; (e3) operating the imaging system to acquire an image of the at least one light stripe at the imaging focus plane; and (e4) analyzing the acquired image of the at least one light stripe in the region of interest and determining the location of at least a portion of the edge feature based on a changing characteristic of the changing light stripe intensity profile along the at least one light stripe. In some embodiments, the user interface may comprise an edge detection video tool comprising a region of interest indicator and the step (c) may comprise defining the region of interest by displaying and configuring the region of interest indicator. In some embodiments, the user interface may comprise an edge detection video tool, and the step (d) may comprise determining the edge direction by aligning a displayed feature of the video tool to correspond to the direction along the edge feature in the region of interest. In some embodiments, in step (e1), orienting the at least one light stripe transverse to the determined edge direction may comprise automatically orienting the at least one light stripe relative to the alignment of the displayed feature of the video tool. In some embodiments, the at least one light stripe may be oriented nominally perpendicular to the displayed feature of the video tool, and a scan line of the video tool may be aligned with the at least one light stripe. In some embodiments, the edge detection video tool may include a region of interest indicator, and the displayed feature that is aligned to correspond to the direction along the edge feature may comprise at least a portion of the region of interest indicator. In some embodiments, the step (e2) may comprise adjusting the brightness of the at least one light stripe such that the brightness of the light stripe is within a detection range of the imaging system, at least in the vicinity of the edge feature.

In some embodiments, the method may further comprise performing the step (e) for at least a first set of light stripes arranged laterally along the edge direction in the region of interest at a first time. In some embodiments, the method may further comprise repeating the step (e) for at least a second set of light stripes arranged laterally along the edge direction in the region of interest at least a second time, wherein the second set of light stripes includes light stripes arranged laterally along the edge direction at different locations than light stripes in the first set of light stripes.

In some embodiments, the light focus stripe plane may be coincident with the imaging focus plane.

In some embodiments, the light stripe focus plane may correspond to a plane of the workpiece surface in the region of interest.

In some embodiments, the edge feature may be curved, the edge direction may follow a corresponding curve, and the first set of light stripes may comprise light stripes which are not parallel to each other.

In some embodiments, the workpiece may be a representative workpiece and the method may be performed in association with a learn mode of operation of the machine vision inspection system, which is used for creating a part program to be used for determining the location of an edge feature on a workpiece that is similar to the representative workpiece.

In some embodiments, the method may be performed in association with a run mode of operation of the machine vision inspection system by executing a part program that includes determining the location of an edge feature on a workpiece that is similar to a representative workpiece used to create a part program.

A machine vision inspection system is provided which is operable to determine a location of an edge feature of a workpiece. The machine vision inspection system, in various embodiments, may comprise a control system; a light stripe projection system; an imaging system operable to focus at an imaging focus plane at a height corresponding to an edge feature in a field of view of the machine vision inspection system; and a user interface operable to define a region of interest including the edge feature and determine an edge direction corresponding to a direction along the edge feature in the region of interest. The light stripe projection system may include an adjustable element that can be adjusted, such that a projected light stripe is oriented transverse to the determined edge direction in the region of interest and extended across the edge feature, and is configurable to project the stripe such that it is focused such that a workpiece surface height change across the edge feature causes a changing stripe intensity profile along the light stripe. The control system may be configured to perform operations comprising: (a) adjusting the adjustable element to orient the light stripe transverse to the determined edge direction in the region of interest and extending across the edge feature; 9b) operating the light stripe projection system to project a light stripe at a light stripe focus plane at a height adjusted to correspond to the edge feature; (c) operating the imaging system to acquire an image of the light stripe at the imaging focus plane at a height corresponding to an edge feature; and (d) analyzing the acquired image of the light stripe in the region of interest and determining the location of at least a portion of the edge feature based on a changing characteristic of the changing light stripe intensity profile along the light stripe. In some embodiments, the machine vision inspection system may comprise an edge detection video tool including a graphical user interface element which is user configurable to set parameters that define the region of interest including the edge feature and the edge direction corresponding to a direction along the edge feature in the region of interest. In some embodiments, the control system may be configured to perform at least the operation(a), based on the parameters set using the edge detection video tool.

In some embodiments, the adjustable element of the light stripe projection system may comprise a controllable spatial light modulator. In some embodiments, the controllable spatial light modulator may comprise one of a controllable LCD array and a controllable micro-minor array.

In some embodiments, the light stripe projection system is configured to use an objective lens of the imaging system to project the light stripe.

In some embodiments, the imaging system may comprise a configurable pupil filter that is located between an objective lens and a camera system of the imaging system at a Fourier plane of the objective lens, and that includes a pupil shape that is configurable such that it is aligned with the light stripe, which spatially filters light from the light stripe. In some embodiments, the pupil filter is provided by a spatial light modulator that modifies at least one of an amplitude and a phase of (a) light which forms the light stripe; or (b) light which is reflected from the workpiece to form the image of the light stripe.

A method for determining a location of an edge feature of a workpiece using a machine vision inspection system is provided. The machine vision inspection system may comprise a control system, a light stripe projection system, an imaging system, and a user interface usable to define a sequence of operations usable to determine the location of the edge feature. The method may comprise: (a) positioning the edge feature in a field of view of a machine vision inspection system; (b) focusing the imaging system at an imaging focus plane at a height corresponding to the edge feature; and (c) determining the edge feature location. Determining the edge feature location may comprise: (c1) operating the light stripe projection system to project at least one light stripe oriented to extend across the edge feature and focused such that a height change across the edge feature causes at least one of a changing width and a changing intensity along the light stripe; (c2) operating the imaging system to acquire an image of the at least one light stripe at the imaging focus plane; and (c3) analyzing the acquired image of the at least one light stripe and determining the location of at least a portion of the edge feature based on a changing characteristic along the light stripe that corresponds to at least one of the changing width and the changing intensity along the light stripe. In some embodiments, (c1) may comprise adjusting the brightness of the at least one light stripe, such that the brightness of the light stripe is within a detection range of the imaging system, at least in the vicinity of the edge feature.

It should be appreciated that the edge detection operations outlined above, which use focused structured illumination, are sensitive to surface height changes across an edge, regardless of other characteristics of the edge that would otherwise make precise edge location difficult when using the conventional edge detection methods. For example, when performing edge detection using conventional illumination (e.g., illumination which is approximately uniformly applied to the field of view) surfaces which have textures or additional features such as a chamfer may diminish the accuracy and reliability of conventional edge detection and/or location operations through unwanted specular reflections or the like, which disturb the brightness gradient across the edge arising from conventional illumination, which is the basis for conventional edge detection and location methods. Therefore the various embodiments outlined herein are aimed at determining an edge location using at least one light stripe which has an intensity which varies based on surface height changes across an edge, to provide edge detection and location operations which may robustly provide sub-pixel edge location accuracy, despite various surface textures and surface features near an edge feature which would be disruptive to conventional edge detection methods.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
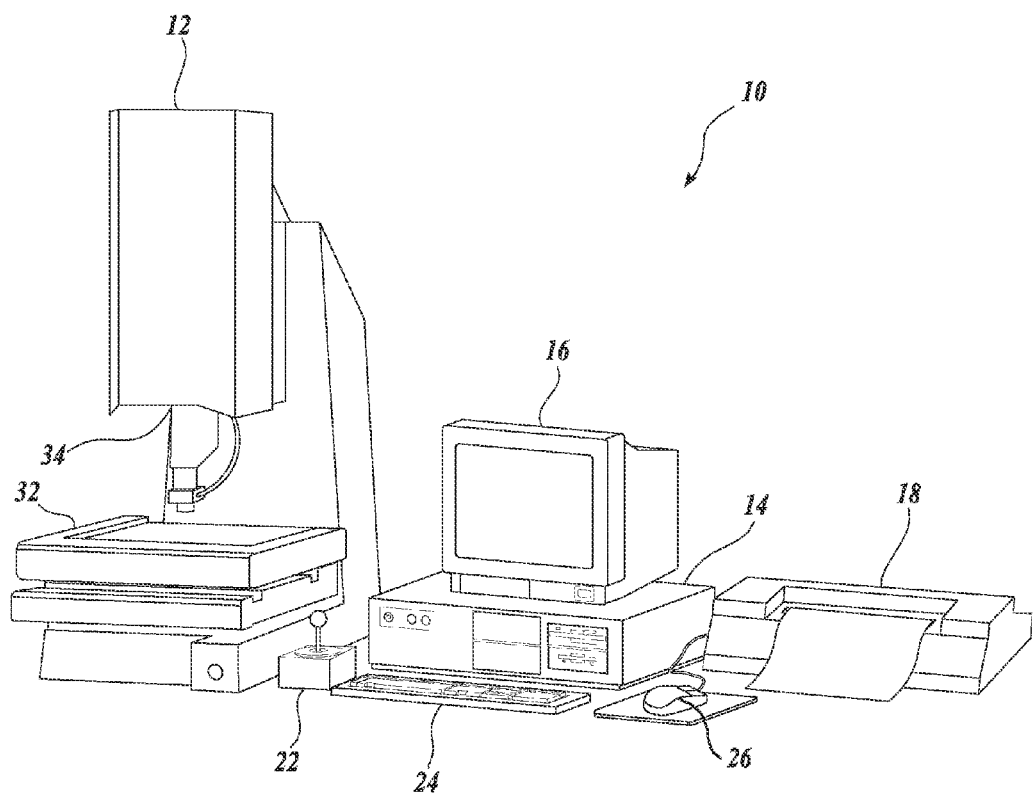
FIG. 1 is a block diagram of one exemplary machine vision inspection system usable in accordance with methods described herein.

FIG. 1 is a block diagram of one exemplary machine vision inspection system 10 usable in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053; 7,324,682; U.S. Patent Application Publication No. 2010/0158343; and U.S. patent application Ser. No. 12/343,383, filed Dec. 23, 2008, and Ser. No. 12/608,943, filed Oct. 29, 2009, which are each incorporated herein by reference in their entireties.

The machine vision inspection system 10 may be configured for imaging and measuring workpiece features including determining edge locations as described below with respect to various embodiments.

Figure 2:
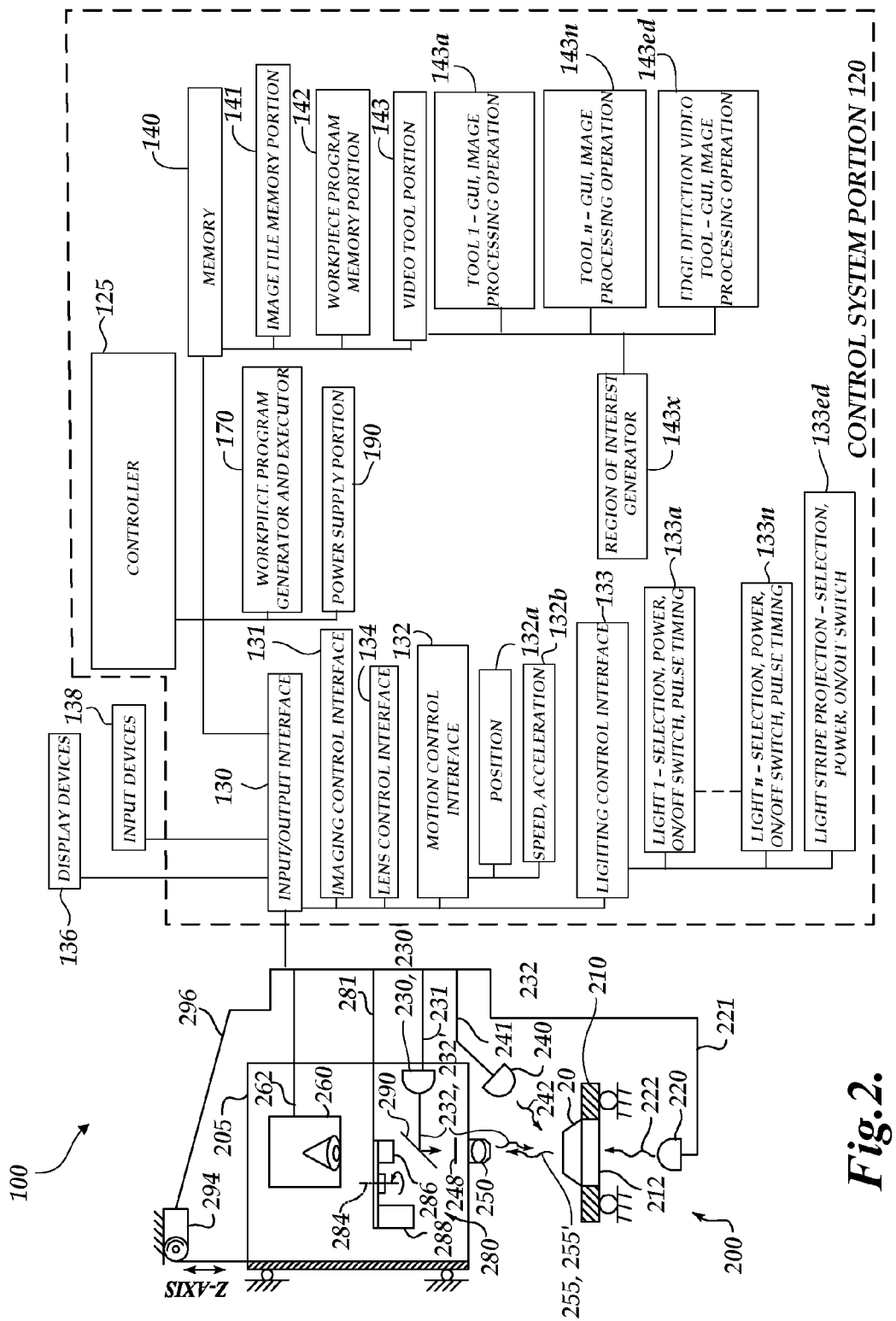
FIG. 2 is a block diagram of a control system portion and a vision components portion of the machine vision inspection system of FIG. 1.

FIG. 2 is a block diagram of a control system portion 120 and a vision components portion 200 of a machine vision inspection system 100. As will be described in more detail below, the control system portion 120 is utilized to control the vision components portion 200. The vision components portion 200 includes an optical assembly portion 205, light sources 220, 230, 230', and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include an optional pupil filter 248 and a turret lens assembly 280 having lenses 286 and 288. Alternatively to the turret lens assembly, a fixed or manually interchangeable magnification-altering lens, or a zoom lens configuration, or the like, may be included. The optical assembly portion 205 is controllably movable along a Z-axis that is generally orthogonal to the X and Y axes, by using a controllable motor 294, as described further below. A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a coaxial light 230, a focused structured light source 230', and a surface light 240 (e.g., a ring light) may emit source light 222, 232, 232', and/or 242, respectively, to illuminate the workpiece or workpieces 20. The light source 230 may emit source light 232 and the focused structured light source 230' may emit source light 232' along a shared path including a beamsplitter 290 and the optional pupil filter 248, as described in greater detail with reference to FIG. 3A. The source light is reflected or transmitted as workpiece light 255 and/or workpiece light 255' and the workpiece light used for imaging passes through the interchangeable objective lens 250, the optional pupil filter 248 and the turret lens assembly 280 and is gathered by the camera system 260. The image of the workpiece(s) 20, captured by the camera system 260, is output on a signal line 262 to the control system portion 120. The light sources 220, 230, 230', and 240 may be connected to the control system portion 120 through signal lines or busses 221, 231, and 241, respectively. To alter the image magnification, the control system portion 120 may rotate the turret lens assembly 280 along axis 284 to select a turret lens, through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z-axis to change the focus of the image of the workpiece 20 captured by the camera system 260. The term Z-axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, the input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a, and a speed/acceleration control element 132b. However, it should be appreciated that in various exemplary embodiments, such elements may be merged and/or indistinguishable. The lighting control interface 133 includes lighting control elements 133a-133n which control, for example, the selection, power, on/off switch, and strobe pulse timing, if applicable, for the various corresponding light sources of the machine vision inspection system 100. The lighting control interface 133 also includes a lighting control element 133ed which controls the selection, power, and on/off switch for the focused structured light source 230'.

The memory 140 includes an image file memory portion 141, a workpiece program memory portion 142 that may include one or more part programs, or the like, and a video tool portion 143. The video tool portion 143 includes tool portion 143a and other similar tool portions (e.g., 143n), as well as an edge detection video tool 143ed which determine the GUI, image processing operation, etc., for each of the corresponding tools. The video tool portion 143 also includes a region of interest generator 143x that supports automatic, semi-automatic, and/or manual operations that define various ROIs that are operable in various video tools included in the video tool portion 143. It should be appreciated that the edge detection video tool 143ed may be configured in one mode to perform conventional edge detection operations using the light source 230 to provide source light 232 and may be additionally configured to perform edge detection operations in another mode using the focused structured light source 230' to provide source light 232'. The latter mode will be described in further detail in later figures.

In general, the memory portion 140 stores data usable to operate the vision system components portion 200 to capture or acquire an image of the workpiece 20 such that the acquired image of the workpiece 20 has desired image characteristics. The memory portion 140 may also store inspection result data, may further store data usable to operate the machine vision inspection system 100 to perform various inspection and measurement operations on the acquired images (e.g., implemented, in part, as video tools), either manually or automatically, and to output the results through the input/output interface 130. The memory portion 140 may also contain data defining a graphical user interface operable through the input/output interface 130.

The signal lines or busses 221, 231, and 241 of the stage light 220, the coaxial light 230, the focused structured light source 230' and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200.

In various exemplary embodiments, when a user utilizes the machine vision inspection system 100 to create a part program for the workpiece 20, the user generates part program instructions either by explicitly coding the instructions automatically, semi-automatically, or manually, using a workpiece programming language and/or by generating the instructions by operating the machine vision inspection system 100 in a learn mode to provide a desired image acquisition training sequence. For example, a training sequence may comprise positioning a workpiece feature of a representative workpiece in the field of view (FOV), setting light levels, focusing or autofocusing, acquiring an image, and providing an inspection training sequence applied to the image (e.g., using video tools). The learn mode operates such that the sequence(s) are captured or recorded and converted to corresponding part program instructions. These instructions, when the part program is executed, will cause the machine vision inspection system to reproduce the trained image acquisition and inspection operations to automatically inspect a workpiece or workpieces matching the representative workpiece used when creating the part program.

These analysis and inspection methods that are used to inspect features in a workpiece image are typically embodied in various video tools included in the video tool portion 143 of the memory 140. Many known video tools, or "tools" for short, are included in commercially available machine vision inspection systems, such as the QUICK VISION® series of vision systems and the associated QVPAK® software, discussed above.

Figure 3A:
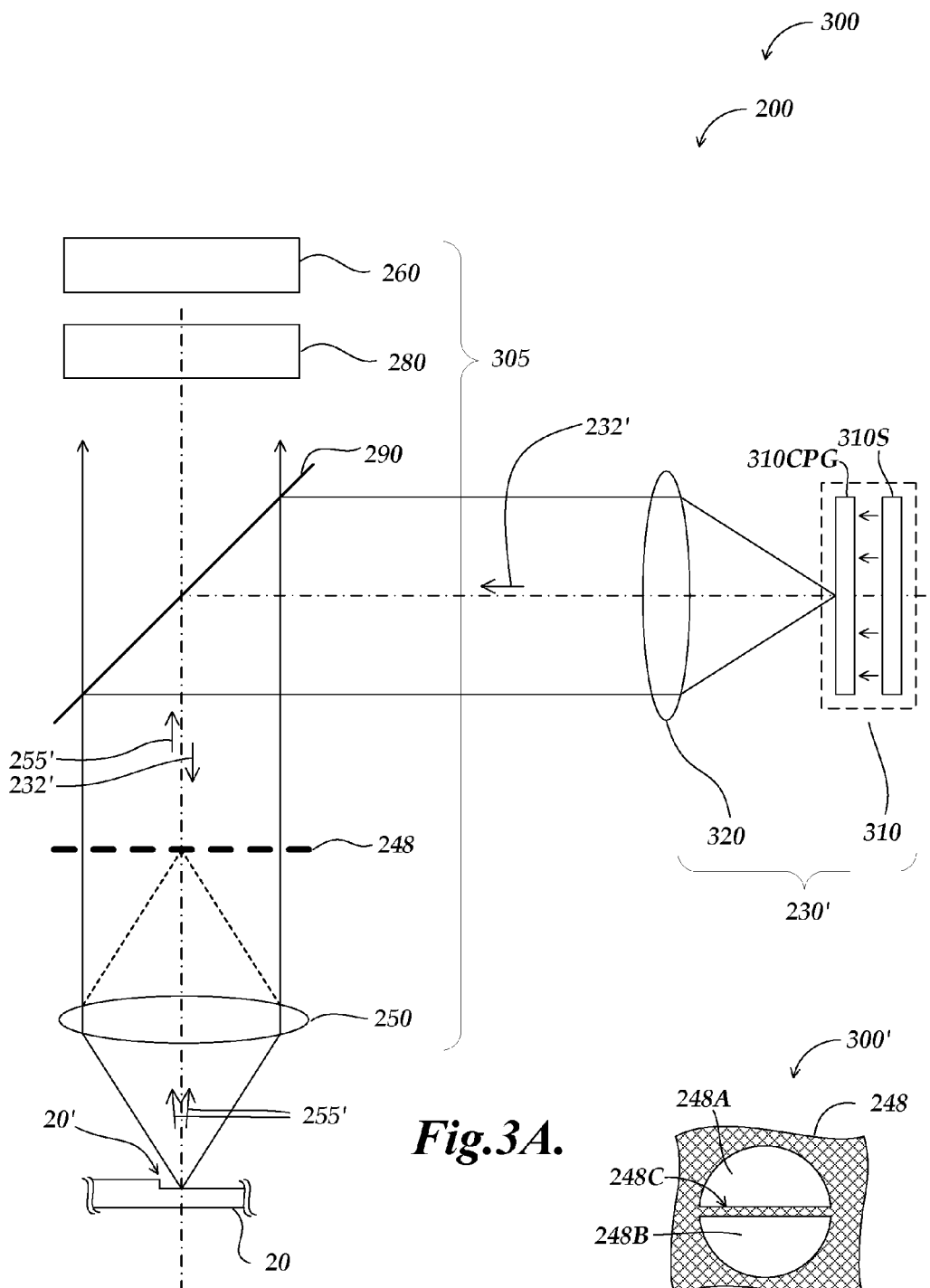
FIG. 3A is a schematic diagram showing one embodiment of the vision components portion of FIG. 2, which shows the operation of a focused structured light source.

FIG. 3A is a schematic diagram 300 showing a portion of one embodiment of the vision components portion 200 (shown in FIG. 2), which shows the operation of the focused structured light source 230'. The vision components portion 200 comprises an imaging system 305 which comprises the camera system 260, the optional pupil filter 248 (located at the Fourier plane of the objective lens 250), the turret lens assembly 280 and the objective lens 250 previously outlined in FIG. 2. FIG. 3A also shows a workpiece 20 which comprises an edge feature 20'. In the embodiment shown in FIG. 3A, the focused structured light source 230' comprises a spatial light modulator arrangement 310 and a lens 320, which work in combination with the objective lens 250 to provide focused structured light (e.g., light stripes) in the field of view. In the embodiment shown schematically in FIG. 3A, the spatial light modulator arrangement 310 comprises a light source 310S and a controllable pattern generator 310CPG. The spatial light modulator arrangement 310 may generally include a light source and various types of controllable pattern generating devices (e.g., an LCD array or a reflective micro minor array), according to known arrangements for providing controllable structured illumination.

In the embodiment shown in FIG. 3A, the focused structured light source 230' comprises a light stripe projection system. In operation, the light source 310S illuminates the controllable pattern generator 310CPG (indicated by arrows) such that the spatial light modulator arrangement 310 emits patterned source light from the controllable pattern generator 310CPG to the lens 320, which outputs the source light 232' such that it creates a focused image of the light pattern produced at the controllable pattern generator 310CPG in the field of view at the workpiece 20, as shown by representative imaging light rays in FIG. 3A. In the illustrated embodiment, the source light 232' is reflected by the beam splitter 290 to the objective lens 250. The objective lens 250 focuses the source light 232' (i.e., a pattern output by the controllable pattern generator 310CPG) on the workpiece 20.

In various embodiments, the controllable pattern generator 310CPG may comprise a controllable LCD array (as shown in FIG. 3A) or a controllable micro-mirror array, or the like. In particular, in various embodiments, the focused image of the light pattern comprises a light stripe, or a plurality of light stripes, and the controllable pattern generator 310CPG is operable to control the orientation of the light stripes in the field of view, and their location, as described further below. The light in the field of view is reflected as workpiece light 255' and the workpiece light 255' used for imaging passes through the interchangeable objective lens 250, the optional pupil filter 248 (if present), and the turret lens assembly 280 and is imaged by the camera system 260. The optional pupil filter 248 will be described in further detail with respect to FIG. 3B.

It will be appreciated that the specific features and elements outlined above for the optical paths of the light stripe projection system are exemplary only and not limiting. Numerous alternatives for illumination and/or imaging in a manner compatible with the methods disclosed herein will be apparent to one of ordinary skill in the art.

Figure 3B:
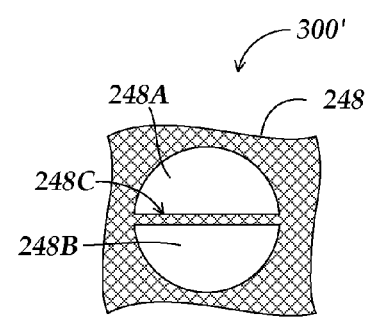
FIG. 3B is a diagram showing further details of a portion of a pupil filter shown in FIG. 3A.

FIG. 3B is a diagram 300' showing further details of a portion of the optional pupil filter 248, also shown in FIG. 3A. In various embodiments, the pupil filter 248 includes a pupil shape that is configurable, such that it is aligned with the at least one light stripe and spatially filters light from the at least one light stripe. In various embodiments, the pupil filter 248 modifies at least one of an amplitude and a phase of (a) light which forms the at least one light stripe, or (b) light which is reflected from the workpiece 20 to form an image of the at least one light stripe on an image sensor of the camera system 260. In the embodiment shown in FIG. 3B, the pupil filter 248 comprises a transmissive portion 248A and a transmissive portion 248B. The transmissive portion 248A and the transmissive portion 248B are separated by an opaque portion 248C. The transmissive portion 248A and the transmissive portion 248B are aligned with the at least one light stripe and are configured to spatially filter the at least one light stripe to enhance the response of the light stripe to the edge feature 20' and to suppress crosstalk between adjacent pixels in the camera system corresponding to points along the at least one light stripe. To suppress crosstalk, the pupil filter 248 is shaped such that a point spread function for a given point along the at least one light stripe which has been spatially filtered by pupil filter 248 spreads light away perpendicularly from the stripe as a level of defocus of the stripe is increased. Thus, the pupil filter 248 is generally controllable to align the pupil filter with the controllable orientation of the light stripes outlined above. In some embodiments the pupil 248 may comprise a spatial light modulator similar to the controllable pattern generator 310CPG.

Figure 4:
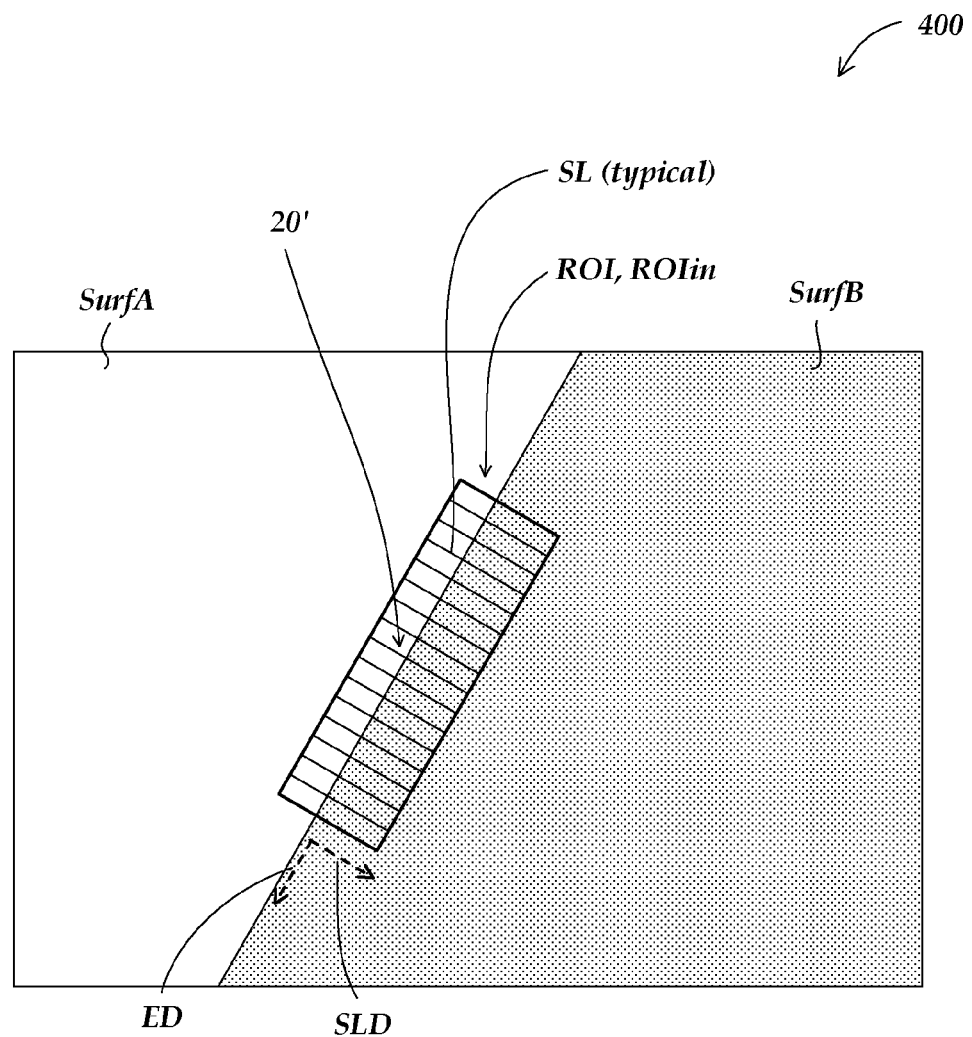
FIG. 4 shows a field of view in a user interface of a machine vision inspection system including a region of interest indicator associated with an edge detection video tool.

FIG. 4 shows a displayed field of view 400 in a user interface of the machine vision inspection system 100, including a region of interest indicator ROIin associated with the edge detection video tool 143ed. In various embodiments of operations for determining the location of an edge feature of a workpiece, the edge feature 20' of the workpiece 20 is positioned in the field of view 400 of the machine vision inspection system 10. The edge feature 20', as shown in FIG. 3A, is an edge between a surface SurfA and a surface SurfB. The surface SurfA has a higher surface plane than the surface plane of SurfB, as will be shown in further detail with respect to FIGS. 5A, 5B, and 5C. The imaging system 305 shown in FIG. 3A is focused at an imaging focus plane at a height corresponding to the edge feature 20', or more specifically to one of the surface SurfA and the surface SurfB. A region of interest ROI is defined using a user interface associated with the edge detection video tool 143ed and displayed with the region of interest indicator ROIin, and the region of interest ROI includes the edge feature 20'. In some embodiments, the edge detection video tool comprises a graphical user interface element which is user configurable to set parameters that define the region of interest ROI, including the edge feature 20' and an edge direction ED which corresponds to a direction along the edge feature 20' in the region of interest ROI. The region of interest ROI may generally be configured and aligned by a user dragging sizing and/or rotation handles (not shown) that appear when the region of interest tool is first implemented to appear in the displayed field of view 400 (e.g., as occurs with known commercially-available machine vision inspection system video tools). The alignment of ROIin may be adjusted such that it is aligned with the edge direction ED, approximately as shown in FIG. 4, such that the parameters of the video tool are used to define the edge direction ED for purposes of machine control and analysis. Finally, a location of a portion of the edge feature 20' is determined. Measurement operations may be performed to determine the location of the edge feature 20' along a scan line SL in a scan line direction SLD, which may be automatically determined based on the alignment of the edge direction ED and/or video tool. Such operations will be outlined with respect to FIGS. 5A, 5B, and 5C.

As shown in FIG. 4, the edge feature 20' is nominally linear. It should be appreciated that the location of an edge feature of a workpiece may also be determined for portions of an edge feature which is curved. Multiple light stripes along multiple non-parallel scan lines may be provided in the region of interest along an edge feature. For example, the edge detection video tool 143ed may be an arc tool or a circle tool for determining edge locations along an edge feature with an arc shape or a circular shape. In general, the operations of the edge detection video tool 143ed may be adapted to any desired shape of an edge feature according to principles outlined and claimed herein. It should be appreciated, that in the case of non-parallel scan lines, the optional pupil filter 248 may not be utilized or may be set up to display a series of differently aligned configurations (requiring capture and analysis of a series of images of stripes), since each pupil filter configuration is capable of effectively filtering along a single stripe direction at a time. The scan lines SL are shown as being parallel linear. However, in general, the edge detection video tool 143ed may define and use scan lines which are not linear and not parallel.

Figure 5A:
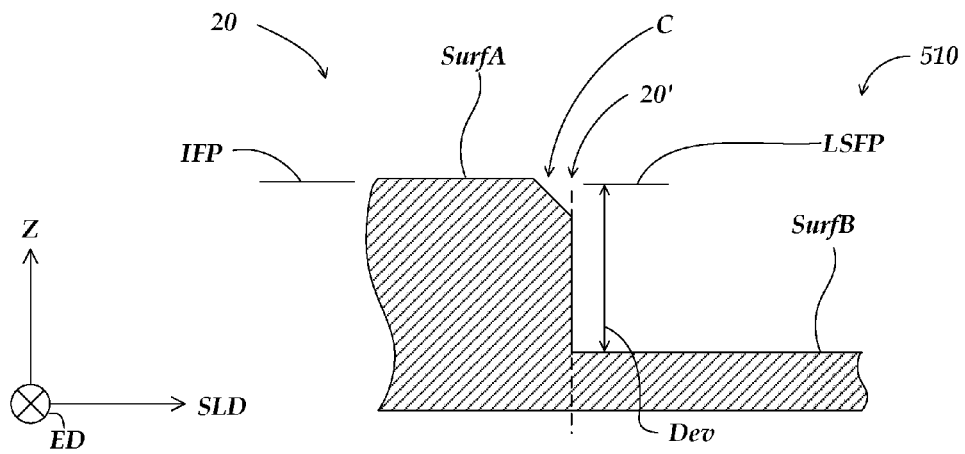
FIG. 5A shows a cross-section view of an edge feature of a workpiece.
Figure 5B:
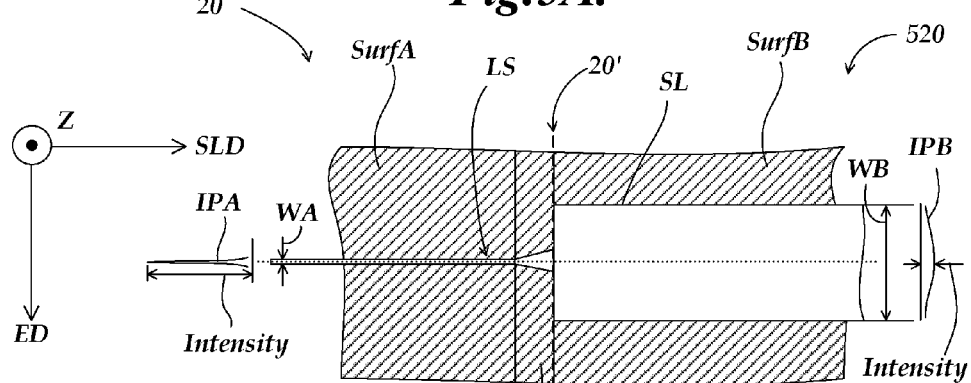
FIG. 5B shows a top view of an edge feature of the workpiece shown in FIG. 5A, including a focused light stripe.
Figure 5C:
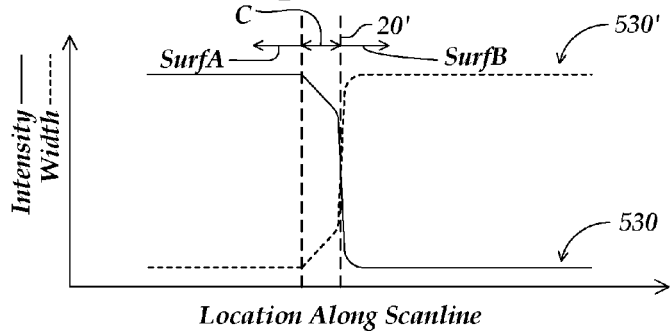
FIG. 5C shows a light stripe intensity profile and a light stripe width associated with the edge feature shown in FIGS. 5A and 5B.

FIG. 5A shows a cross-section view 510 of the edge feature 20', FIG. 5B shows a top view 520 of the edge feature 20', and FIG. 5C shows changing light stripe intensity profile characteristics, in particular the changing intensity 530 (e.g., a peak intensity or other representative intensity) and changing light stripe width 530' associated with the changing transverse stripe intensity profile across the edge feature 20'. FIGS. 5A, 5B, and 5C show further detail of operations for determining the location of an edge feature of a workpiece with a machine vision inspection system outlined previously with respect to FIG. 4. Adjacent to the edge feature 20' is a chamfer C.

In various embodiments, the focused structured light source 230' of FIG. 3A comprises a light stripe projection system. The focused structured light source 230' is operated to project at least one light stripe (e.g., a light stripe LS shown in FIG. 5B), oriented transverse to the edge direction ED in the region of interest ROI (shown in FIG. 4), and extending across the edge feature 20'. The light stripe LS may be oriented based on parameters set using the edge detection video tool 143ed (e.g., as outlined above). In general, the light stripe LS may be aligned with scan line direction SLD (or vice versa) and in the embodiment shown in FIGS. 5A, 5B, and 5C, the scan line SL of the edge detection video tool 143ed is aligned with a light stripe, such that the scan line defines and/or provides image brightness data along the light stripe. It should be appreciated that the scan line direction SLD does not necessarily correspond to a row or column of pixels in the camera system 260. The focused structured light source 230' is operated in response to the lighting control element 133ed in accordance with parameters defined by the edge detection video tool 143ed to focus the light stripe LS at a height corresponding to the edge feature 20' (i.e., the light stripe focus plane LSFP in FIG. 5A), such that a height change across the edge feature produces a changing stripe intensity profile along the light stripe, as described below.

The imaging system 305 is operated to acquire an image of the light stripe LS at an imaging focus plane IFP shown in FIG. 5A. In the embodiment shown in FIG. 5A, the imaging focus plane IFP is at the same height as the surface SurfA. The acquired image of the light stripe LS is analyzed in the region of interest ROI, and the location of at least a portion of the edge feature 20' is determined based on a changing characteristic of the changing light stripe intensity profile 530 (shown in FIG. 5C) along the light stripe LS. For example, FIG. 5B shows two exemplary stripe intensity profiles (transverse intensity profiles) at two respective locations along the light stripe. It will be understood that the stripe intensity profile IPA results from a stripe portion that is well focused at the height of surface SurfA and has a relatively large peak intensity and a narrow width. The stripe intensity profile IPB results from a stripe portion that is poorly focused at the height of surface SurfB and has a relatively low peak intensity and a large width.

Thus, generally, the light stripe LS has a width and/or a nominal stripe brightness or intensity at a given point along the stripe, which vary with surface height due to defocus. For example, in the embodiment shown in FIG. 5A and FIG. 5B, along the surface SurfA the light stripe LS is focused at the light stripe focus plane LSFP which is coincident with the surface height of the surface SurfA. In general, the light stripe focus plane LSFP may correspond to a plane of the workpiece surface in the region of interest ROI (e.g., the surface SurfA or the surface SurfB). As shown in FIG. 5B, because the light stripe LS is focused at the surface SurfA, the light stripe LS has a width WA along the surface SurfA which is at a minimum and an intensity along the surface SurfA which is at a maximum. In some embodiments, such as that shown in FIG. 5A, the light stripe focus plane LSFP is coincident with the imaging focus plane IFP. Along the surface SurfB, which has a surface height deviation Dev from the laser stripe focus plane, the light stripe LS has a larger width WB due to defocus. Therefore, for a given point along the light stripe LS along the surface SurfB, there is a lower image intensity. Along the chamfer C, the light stripe LS slowly becomes wider due to increasing defocus along the scan line direction SLD. Proximate to the location of the edge feature 20' between the chamfer C and the surface SurfB, the changing intensity 530 of the light stripe LS shows a sharp gradient along the scan line direction, as illustrated in FIG. 5C. Using conventional machine vision inspection system illumination with conventional edge detection image processing operations may be problematic in the presence of the chamfer C or other edge imperfections, or in embodiments where the surface SurfA is highly textured. Specular reflections and surface reflectivity variations may interfere with the reliability and accuracy of edge detection image processing operations. This may cause the edge detection video tool 143ed to fail. However, using the light stripe LS in accordance with the operations described herein provides a means for determining the location of an edge feature which is robust to surface features, such as a chamfer, bevel, rounding, edge imperfections, highly textured surfaces, and/or surface reflectivity variations.

It should be appreciated that the light stripe LS may be analyzed according to conventional edge detection image processing operations; and, therefore, the operations for determining a location of an edge feature of a workpiece may be conveniently implemented in a machine vision inspection system. Such a machine vision inspection system comprises: a control system (e.g., the control system portion 120), a light stripe projection system (e.g., the focused structured light source 230'), an imaging system (e.g., the imaging system 305) operable to focus at an imaging focus plane (e.g., the imaging focal plane IFP) at a height corresponding to an edge feature (e.g., the edge feature 20') in a field of view of the machine vision inspection system (e.g., the field of view 400), and a user interface operable to define a region of interest (e.g., the region of interest ROI) including an edge feature, and to determine an edge direction (e.g., the edge direction ED) corresponding to a direction along the edge feature in the region of interest. The light stripe projection system includes an adjustable element (e.g., the spatial light modulator arrangement 310) that can be adjusted such that a projected light stripe is oriented transverse to the determined edge direction in the region of interest and extending across the edge feature. The light stripe projection system is configurable to project the light stripe such that it is focused such that a workpiece surface height change across the edge feature causes a changing stripe intensity profile along the light stripe (e.g., as represented by the changing intensity 530, and/or the changing width 530', along the chamfer C and between the chamfer C and the surface SurfB). The control system is configured to perform various operations. The operations comprise adjusting the adjustable element to orient the light stripe transverse to the determined edge direction in the region of interest and extending across the edge feature, operating the light stripe projection system to project a light stripe (e.g., the light stripe LS) at a light stripe focus plane (e.g., the light stripe focus plane LSFP) at a height adjusted to correspond to the edge feature, operating the imaging system to acquire an image of the light stripe at the imaging focus plane at a height corresponding to an edge feature, and analyzing the acquired image of the light stripe in the region of interest and determining the location of at least a portion of the edge feature based on a changing characteristic of the changing light stripe intensity profile along the light stripe, as outlined above.

Figure 6:
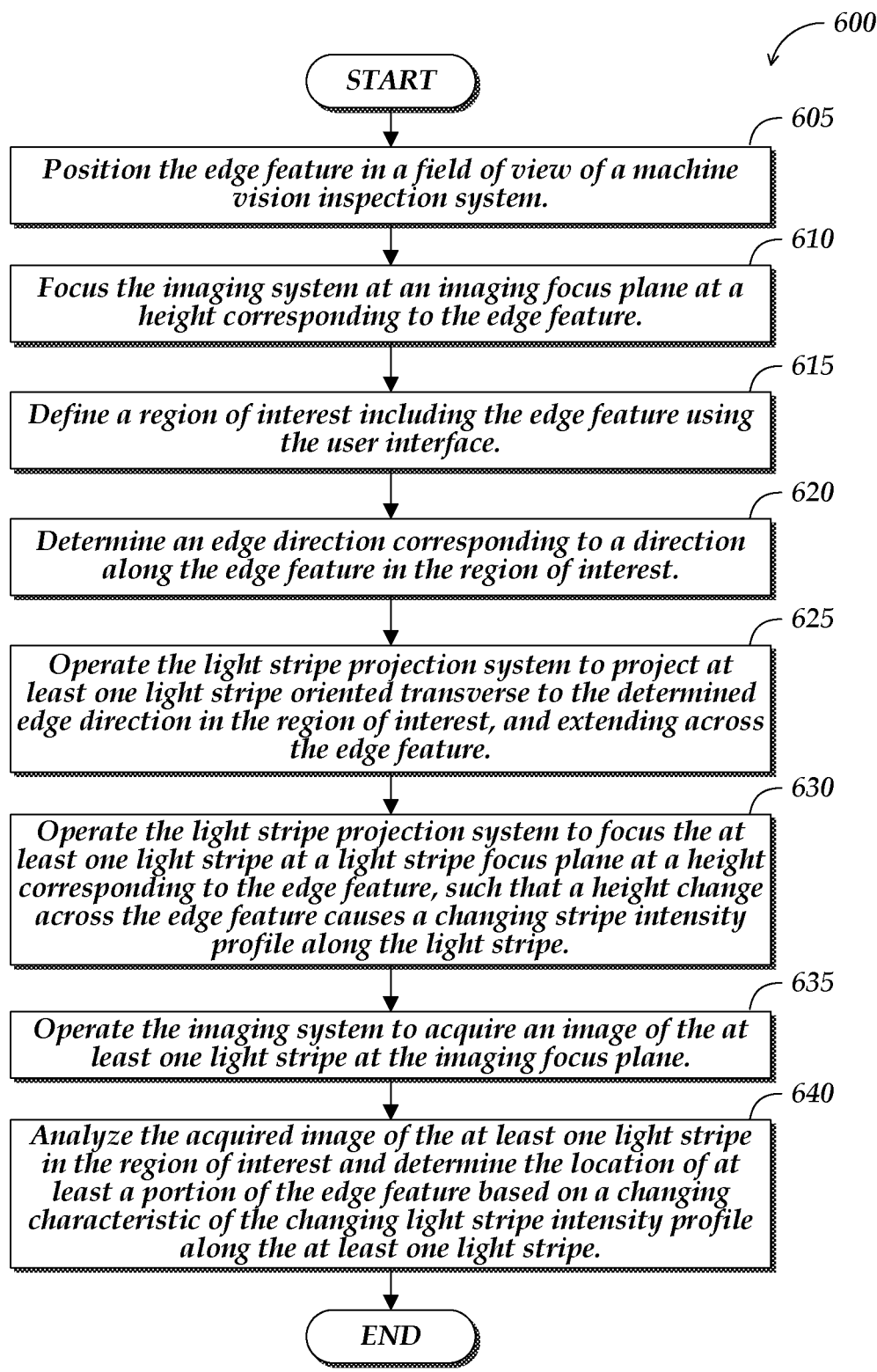
FIG. 6 is a flow diagram outlining a method and routine for determining the location of an edge feature of a workpiece using a machine vision inspection system according to one embodiment of the method disclosed herein.

FIG. 6 shows a flow diagram 600 outlining a method and routine for determining a location of an edge feature of a workpiece using a machine vision inspection system, the machine vision inspection system comprising a control system, a light stripe projection system, an imaging system, and a user interface usable to define a sequence of operations usable to determine the location of the edge feature.

In one embodiment, the method shown in FIG. 6 may be implemented, at least in part by a user by selecting and operating the edge detection video tool 143ed shown in FIG. 2 and/or as described with reference to the operations described in FIGS. 3, 4, 5A, 5B, and 5C. In other embodiments, the method may be implemented using various known tools and/or programming operations.

The routine starts, and at a block 605, the edge feature is positioned in a field of view of a machine vision inspection system. For example, in FIG. 4 the edge feature 20' is positioned in the field of view 400 of the machine vision inspection system 100.

At a block 610, the imaging system is focused at an imaging focus plane at a height corresponding to the edge feature. For example, the imaging system 305 of FIG. 3 is focused at an imaging focus plane IFP at a height corresponding to the edge feature 20' in FIG. 5A.

At a block 615, a region of interest is defined including the edge feature using the user interface. For example, the region of interest ROI is defined including the edge feature 20' by configuring the region of interest indicator ROIin in the user interface shown in FIG. 4.

At a block 620, an edge direction is determined corresponding to a direction along the edge feature in the region of interest. For example, the edge direction ED corresponding to a direction along the edge feature 20' in the region of interest ROI in FIG. 4 may be determined for purposes of machine control and/or analysis by aligning a displayed feature of a video tool with the direction along the edge feature. In some embodiments, the edge detection video tool includes a region of interest indicator, and the displayed feature that is aligned to correspond to the direction along the edge feature comprises at least a portion of the region of interest indicator. It should be appreciated that in some embodiments, the steps outlined at the blocks 615 and 620 may be performed automatically based on image processing performed by the machine vision inspection system, or in various alternative embodiments, the steps outlined at the blocks 615 and 620 may be performed manually. In yet other embodiments and/or specific applications, the steps outlined at the blocks 615 and 620 need not be performed explicitly; and, therefore, alternative embodiments of the routine 600 may omit the blocks 615 and 620.

At the blocks 625, 630, 635, and 640, the edge feature location is determined. At a block 625, the light stripe projection system is operated to project at least one light stripe oriented transverse to the determined edge direction in the region of interest, and extending across the edge feature. In some embodiments, the user interface comprises an edge detection video tool comprising a region of interest indicator and defining a region of interest comprises defining the region of interest by displaying and configuring the region of interest indicator. For example, as outlined in FIG. 4, the edge detection video tool 143ed comprises a region of interest indicator ROIin which may be used to define the region of interest ROI. In some embodiments, the user interface comprises an edge detection video tool, and determining an edge direction comprises aligning a displayed feature of the video tool to correspond to the direction along the edge feature in the region of interest. In some embodiments, orienting the at least one light stripe transverse to the determined edge direction comprises automatically orienting the at least one light stripe relative to the alignment of the displayed feature of the video tool, e.g., the edge detection video tool 143ed outlined in FIG. 4. In some embodiments, the at least one light stripe is nominally perpendicular to the displayed feature of the video tool and a scan line of the video tool is aligned with the at least one light stripe.

At a block 630, the light stripe projection system is operated to focus the at least one light stripe at a light stripe focus plane at a height corresponding to the edge feature, such that a height change across the edge feature causes a changing stripe intensity profile along the light stripe. In some embodiments, the light stripe focus plane is coincident with the imaging focus plane. For example, in the configuration shown in FIG. 5A, the light stripe focus plane LSFP is coincident with the imaging focus plane IFP. This may be particularly advantageous when the imaging objective lens is used to focus the light stripes in the field of view, as shown in FIG. 3A. In some embodiments, the light stripe focus plane corresponds to a plane of the workpiece surface in the region of interest. For example, in the configuration shown in FIG. 5A, the light stripe plane LSFP corresponds to the plane of the workpiece surface SurfA, and in particular, the light stripe focus plane LSFP is coincident with the workpiece surface SurfA.

At a block 635, the imaging system is operated to acquire an image of the at least one light stripe at the imaging focus plane.

At a block 640, the acquired image of the at least one light stripe in the region of interest is analyzed and the location of at least a portion of the edge feature is determined based on a changing characteristic of the changing light stripe intensity profile along the at least one light stripe, and the routine ends. In some embodiments, the steps at blocks 625, 630, 635, and 640 may be performed for at least a first set of light stripes arranged laterally along the edge direction in the region of interest at a first time. Additionally, in some embodiments, the steps at blocks 625, 630, 635, and 640 may be repeated for at least a second set of light stripes arranged laterally along the edge direction in the region of interest at a second time, wherein the second set of light stripes includes light stripes arranged laterally along the edge direction at different locations than light stripes in the first set of light stripes. This allows for a higher density of sampling of edge feature locations along the edge direction while avoiding crosstalk between adjacent light stripes. In some embodiments, the edge feature is curved and the edge direction follows a corresponding curve and the first set of light stripes comprises light stripes which are not parallel to each other. The routine may be adapted to various shapes of edge features, for example an arc or a circle, where light stripes that are oriented transverse to the edge direction at various locations are not parallel to one another. Also, similarly oriented light stripes can be analyzed in separate sets, each set filtered by a specific optional pupil filter configuration that is best matched to the dominant direction in the set.

In some embodiments, the workpiece is a representative workpiece and the method is performed in association with a learn mode of operation of the machine vision inspection system, which is used for creating a part program to be used for determining the location of an edge feature on a workpiece that is similar to the representative workpiece. In other embodiments, the method is performed in association with a run mode of operation of the machine vision inspection system by executing a part program that includes determining the location of an edge feature on a workpiece that is similar to a representative workpiece used to create a part program.

It should be appreciated that the workpiece may be illuminated with conventional illumination for defining the region of interest at the block 615 and determining the edge direction at the block 620. At the blocks 625, 630, 635, and 640, the conventional illumination may be omitted such that the workpiece is illuminated with only the at least one light stripe.

It should be appreciated that the systems and methods disclosed herein provide a more reliable and accurate edge detection method than previously practiced edge detection methods in the presence of problematic surface textures and features adjacent to an edge feature. While various preferred and exemplary embodiments of the invention have been illustrated and described, it will be appreciated that various changes can be made therein without departing from the spirit and scope of the invention.

The embodiments of the invention in which an exclusive property or privilege is claimed are defined as follows:

1. A method for determining a location of an edge feature of a three-dimensional workpiece using a machine vision inspection system, wherein the machine vision inspection system comprises a control system, a light stripe projection system, an imaging system, and a user interface usable to define a sequence of operations usable to determine the location of the edge feature, the method comprising:
   (a) positioning the edge feature of the three-dimensional workpiece in a field of view of the machine vision inspection system;
   (b) focusing the imaging system at an imaging focus plane at a height corresponding to the edge feature;
   (c) defining a region of interest including the edge feature using the user interface;
   (d) determining an edge direction corresponding to a direction along the edge feature in the region of interest; and
   (e) determining the edge feature location, wherein determining the edge feature location comprises:
      (e1) operating the light stripe projection system to project at least one light stripe having a longitudinal axis oriented transverse to the determined edge direction in the region of interest, and extending across the edge feature;
      (e2) operating the light stripe projection system to focus the at least one light stripe at a light stripe focus plane at a height corresponding to the edge feature such that a surface height change across the edge feature causes a changing light stripe intensity profile along the light stripe due to defocus, which varies with the edge feature surface height along the light stripe without changing the orientation of the longitudinal axis of the light stripe;
      (e3) operating the imaging system to acquire an image of the at least one light stripe at the imaging focus plane; and
      (e4) analyzing the acquired image of the at least one light stripe in the region of interest and determining the location of at least a portion of the edge feature based on a changing characteristic of the changing light stripe intensity profile along the at least one light stripe.

2. The method of claim 1, wherein the light stripe focus plane is coincident with the imaging focus plane.

3. The method of claim 1, wherein the light stripe focus plane corresponds to a plane of the workpiece surface in the region of interest.

4. The method of claim 1, wherein the user interface comprises an edge detection video tool comprising a region of interest indicator and the step (c) comprises defining the region of interest by displaying and configuring the region of interest indicator.

5. The method of claim 1, wherein the user interface comprises an edge detection video tool and the step (d) comprises determining the edge direction by aligning a displayed feature of the video tool to correspond to the direction along the edge feature in the region of interest.

6. The method of claim 5, wherein in step (e1) orienting the at least one light stripe transverse to the determined edge direction comprises automatically orienting the at least one light stripe relative to the alignment of the displayed feature of the video tool.

7. The method of claim 6, wherein the at least one light stripe is oriented nominally perpendicular to the displayed feature of the video tool, and a scan line of the video tool is aligned with the at least one light stripe.

8. The method of claim 5, wherein the edge detection video tool includes a region of interest indicator, and the displayed feature that is aligned to correspond to the direction along the edge feature comprises at least a portion of the region of interest indicator.

9. The method of claim 1, wherein the step (e2) comprises adjusting the brightness of the at least one light stripe such that the brightness of the light stripe is within a detection range of the imaging system, at least in the vicinity of the edge feature.

10. The method of claim 1, further comprising performing the step (e) for at least a first set of light stripes arranged laterally along the edge direction in the region of interest at a first time.

11. The method of claim 10, further comprising repeating the step (e) for at least a second set of light stripes arranged laterally along the edge direction in the region of interest at a second time, wherein the second set of light stripes includes light stripes arranged laterally along the edge direction at different locations than light stripes in the first set of light stripes.

12. The method of claim 10, wherein the edge feature is curved and the edge direction follows a corresponding curve and the first set of light stripes comprises light stripes which are not parallel to each other.

13. The method of claim 1, wherein the workpiece is a representative workpiece and the method is performed in association with a learn mode of operation of the machine vision inspection system, which is used for creating a part program to be used for determining the location of an edge feature on a workpiece that is similar to the representative workpiece.

14. The method of claim 1, wherein the method is performed in association with a run mode of operation of the machine vision inspection system by executing a part program that includes determining the location of an edge feature on a workpiece that is similar to a representative workpiece used to create the part program.

15. A machine vision inspection system operable to determine a location of an edge feature of a three-dimensional workpiece, the machine vision inspection system comprising:
   a control system;
   a light stripe projection system;
   an imaging system operable to focus at an imaging focus plane at a height corresponding to an edge feature of the three-dimensional workpiece in a field of view of the machine vision inspection system; and
   a user interface operable to define a region of interest including the edge feature and determine an edge direction corresponding to a direction along the edge feature in the region of interest, wherein:
   the light stripe projection system:
      includes an adjustable element that can be adjusted such that a projected light stripe having a longitudinal axis is oriented transverse to the determined edge direction in the region of interest and extends across the edge feature, and
      is configurable to project the light stripe such that it is focused such that a workpiece surface height change across the edge feature causes a changing light stripe intensity profile along the light stripe due to defocus, which varies with the edge feature surface height along the light stripe without changing the orientation of the longitudinal axis of the light stripe; and
   the control system is configured to perform operations comprising:
      (a) adjusting the adjustable element to orient the light stripe transverse to the determined edge direction in the region of interest and extending across the edge feature;
      (b) operating the light stripe projection system to project a light stripe at a light stripe focus plane at a height adjusted to correspond to the edge feature;
      (c) operating the imaging system to acquire an image of the light stripe at the imaging focus plane at a height corresponding to an edge feature; and
      (d) analyzing the acquired image of the light stripe in the region of interest and determining the location of at least a portion of the edge feature based on a changing characteristic of the changing light stripe intensity profile along the light stripe.

16. The machine vision inspection system of claim 15, wherein the adjustable element of the light stripe projection system comprises a controllable spatial light modulator.

17. The machine vision inspection system of claim 16, wherein the controllable spatial light modulator comprises one of a controllable LCD array and a controllable microminor array.

18. The machine vision inspection system of claim 15, wherein the light stripe projection system is configured to use an objective lens of the imaging system to project the light stripe.

19. The machine vision inspection system of claim 15, wherein the machine vision inspection system comprises an edge detection video tool including a graphical user interface element which is user configurable to set parameters that define the region of interest including the edge feature and the edge direction corresponding to a direction along the edge feature in the region of interest.

20. The machine vision inspection system of claim 19, wherein the control system is configured to perform at least the operation (a) based on the parameters set using the edge detection video tool.

21. The machine vision inspection system of claim 15, wherein the imaging system comprises a configurable pupil filter that is located between an objective lens and a camera of the imaging system at a Fourier plane of the objective lens, and that includes a pupil shape that is configurable such that it is aligned with the light stripe, which spatially filters light from the light stripe.

22. The machine vision inspection system of claim 21, wherein the pupil filter is provided by a spatial light modulator that modifies at least one of an amplitude and a phase of (a) light which forms the light stripe, or (b) light which is reflected from the workpiece to form the image of the light stripe on an image sensor of the camera system.

23. A method for determining a location of an edge feature of a three-dimensional workpiece using a machine vision inspection system, wherein the machine vision inspection system comprises a control system, a light stripe projection system, an imaging system, and a user interface usable to define a sequence of operations usable to determine the location of the edge feature, the method comprising:
   (a) positioning the edge feature of the three-dimensional workpiece in a field of view of a machine vision inspection system;
   (b) focusing the imaging system at an imaging focus plane at a height corresponding to the edge feature; and
   (c) determining the edge feature location, wherein determining the edge feature location comprises:
      (c1) operating the light stripe projection system to project at least one light stripe having a longitudinal axis, oriented to extend across the edge feature, and focused such that a height change across the edge feature causes at least one of a changing width and a changing intensity along the light stripe due to defocus, which varies with the edge feature surface height along the light stripe without changing the orientation of the longitudinal axis of the light stripe;

(c2) operating the imaging system to acquire an image of the at least one light stripe at the imaging focus plane; and (c3) analyzing the acquired image of the at least one light stripe and determining the location of at least a portion of the edge feature based on a changing characteristic along the light stripe that corresponds to at least one of the changing width and the changing intensity along the light stripe.

24. The method of claim 23, wherein (c1) comprises adjusting the brightness of the at least one light stripe such that the brightness of the light stripe is within a detection range of the imaging system, at least in the vicinity of the edge feature.

* * * * *

UNITED STATES PATENT AND TRADEMARK OFFICE
CERTIFICATE OF CORRECTION

PATENT NO. : 8,773,526 B2
APPLICATION NO. : 12/972386
DATED : July 8, 2014
INVENTOR(S) : R. K. Bryll It is certified that error appears in the above-identified patent and that said Letters Patent is hereby corrected as shown below:

In the Claims

| COLUMN | LINES | ERROR |
|---|---|---|
| Column 18 | 17/18 | Change "micro-minor" to --micro-mirror-- |

Signed and Sealed this
Seventeenth Day of March, 2015

Michelle K. Lee
*Director of the United States Patent and Trademark Office*